US007215997B2

(12) United States Patent
Yu et al.

(10) Patent No.: US 7,215,997 B2
(45) Date of Patent: May 8, 2007

(54) DYNAMIC DEVICE THERAPY CONTROL FOR TREATING POST MYOCARDIAL INFARCTION PATIENTS

(75) Inventors: Yinghong Yu, Maplewood, MN (US); Jiang Ding, Maplewood, MN (US); Joseph M. Pastore, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 398 days.

(21) Appl. No.: 10/744,900

(22) Filed: Dec. 22, 2003

(65) Prior Publication Data

US 2005/0137631 A1    Jun. 23, 2005

(51) Int. Cl.
*A61N 1/365* (2006.01)
(52) U.S. Cl. .......................................... 607/18; 607/19
(58) Field of Classification Search ...................... None
See application file for complete search history.

(56) References Cited

U.S. PATENT DOCUMENTS

| | | | |
|---|---|---|---|
| 4,354,497 A | 10/1982 | Kahn | |
| 4,686,987 A | 8/1987 | Salo et al. | |
| 4,872,459 A | 10/1989 | Pless et al. | |
| 4,880,005 A | 11/1989 | Pless et al. | |
| 4,922,907 A | 5/1990 | Hedin et al. | |
| 4,928,688 A | 5/1990 | Mower | |
| 4,930,075 A | 5/1990 | Kortas | |
| 4,945,909 A | 8/1990 | Fearnot et al. | |
| 4,981,139 A | 1/1991 | Pfohl | |
| 5,014,698 A | 5/1991 | Cohen | |
| 5,109,842 A | 5/1992 | Adinolfi | |
| 5,113,869 A | 5/1992 | Nappholz et al. | |
| 5,135,004 A | 8/1992 | Adams et al. | |
| 5,156,149 A | 10/1992 | Hudrlik | |
| 5,158,079 A | 10/1992 | Adams et al. | |
| 5,168,869 A | 12/1992 | Chirife | |
| 5,174,289 A | 12/1992 | Cohen | |

(Continued)

FOREIGN PATENT DOCUMENTS

EP    0054138    6/1982

(Continued)

OTHER PUBLICATIONS

Auricchio, "Cardiac Resynchronization Therapy Restores Optimal Atrioventricular Mechanical Timing in Heart Failure Patients with Ventricular Conduction Delay", *Journal of the American College of Cardiology*, vol. 39, No. 7, (Apr. 3, 2002), 1163-1169.

(Continued)

*Primary Examiner*—Carl Layno
(74) *Attorney, Agent, or Firm*—Schwegman, Lundberg, Woessner & Kluth, P.A.

(57) ABSTRACT

A cardiac rhythm management system includes an implantable device executing a dynamic pacing algorithm after an myocardial infarction (MI) event. The dynamic pacing algorithm dynamically adjusts one or more pacing parameters based on a person's gross physical activity level. Examples of the one or more pacing parameters include atrioventricular pacing delays and pacing channels/sites. The dynamic pacing algorithm provides for improved hemodynamic performance when a person's metabolic need is high, and post MI remodeling control when the person's metabolic need is low.

71 Claims, 6 Drawing Sheets

U.S. PATENT DOCUMENTS

| | | |
|---|---|---|
| 5,179,947 A | 1/1993 | Meyerson et al. |
| 5,179,949 A | 1/1993 | Chirife |
| 5,199,428 A | 4/1993 | Obel et al. |
| 5,233,985 A | 8/1993 | Hudrlik |
| 5,267,560 A | 12/1993 | Cohen |
| 5,269,301 A | 12/1993 | Cohen |
| 5,318,595 A | 6/1994 | Ferek-Petric et al. |
| 5,330,511 A | 7/1994 | Boute |
| 5,331,768 A | 7/1994 | Takeuchi |
| 5,334,222 A | 8/1994 | Salo et al. |
| 5,370,665 A | 12/1994 | Hudrlik |
| 5,514,161 A | 5/1996 | Limousin |
| 5,514,163 A | 5/1996 | Markowitz et al. |
| 5,527,347 A | 6/1996 | Shelton et al. |
| 5,531,768 A | 7/1996 | Alferness |
| 5,534,016 A | 7/1996 | Boute |
| 5,549,650 A | 8/1996 | Bornzin et al. |
| 5,554,177 A | 9/1996 | Kieval et al. |
| 5,584,867 A | 12/1996 | Limousin et al. |
| 5,584,868 A | 12/1996 | Salo et al. |
| 5,609,612 A | 3/1997 | Plicchi et al. |
| 5,626,620 A | 5/1997 | Kieval et al. |
| 5,626,623 A | 5/1997 | Kieval et al. |
| 5,628,777 A | 5/1997 | Moberg et al. |
| 5,674,256 A | 10/1997 | Carlson |
| 5,674,259 A | 10/1997 | Gray |
| 5,683,429 A | 11/1997 | Mehra |
| 5,690,689 A | 11/1997 | Sholder |
| 5,700,283 A | 12/1997 | Salo |
| 5,713,930 A | 2/1998 | van der Veen et al. |
| 5,716,383 A | 2/1998 | Kieval et al. |
| 5,749,906 A | 5/1998 | Kieval et al. |
| 5,792,195 A | 8/1998 | Carlson et al. |
| 5,797,970 A | 8/1998 | Pouvreau |
| 5,800,471 A | 9/1998 | Baumann |
| 5,824,019 A | 10/1998 | Rueter et al. |
| 5,836,987 A | 11/1998 | Baumann et al. |
| 5,851,226 A | 12/1998 | Skubitz et al. |
| 5,935,081 A | 8/1999 | Kadhiresan |
| 5,935,160 A | 8/1999 | Auricchio et al. |
| 5,991,668 A | 11/1999 | Leinders et al. |
| 6,021,350 A | 2/2000 | Mathson |
| 6,038,483 A | 3/2000 | KenKnight et al. |
| 6,044,298 A | 3/2000 | Salo et al. |
| 6,044,299 A | 3/2000 | Nilsson |
| 6,058,329 A | 5/2000 | Salo et al. |
| 6,066,094 A | 5/2000 | Ben-Haim |
| 6,108,577 A | 8/2000 | Benser |
| 6,112,117 A | 8/2000 | KenKnight et al. |
| 6,128,526 A | 10/2000 | Stadler et al. |
| 6,144,880 A | 11/2000 | Ding et al. |
| 6,151,524 A | 11/2000 | Krig et al. |
| 6,152,955 A | 11/2000 | KenKnight et al. |
| 6,208,900 B1 | 3/2001 | Ecker et al. |
| 6,208,901 B1 | 3/2001 | Hartung |
| 6,223,082 B1 | 4/2001 | Bakels et al. |
| 6,272,377 B1 | 8/2001 | Sweeney et al. |
| 6,273,856 B1 | 8/2001 | Sun et al. |
| 6,280,389 B1 | 8/2001 | Ding et al. |
| 6,311,089 B1 | 10/2001 | Mann et al. |
| 6,351,673 B1 | 2/2002 | Ding et al. |
| 6,360,127 B1 | 3/2002 | Ding et al. |
| 6,409,675 B1 | 6/2002 | Turcott |
| 6,430,439 B1 | 8/2002 | Wentkowski et al. |
| 6,438,421 B1 | 8/2002 | Stahmann et al. |
| 6,449,510 B1 | 9/2002 | Albers et al. |
| 6,477,406 B1 | 11/2002 | Turcott |
| 6,480,733 B1 | 11/2002 | Turcott |
| 6,480,742 B2 | 11/2002 | Stahmann et al. |
| 6,507,756 B1 | 1/2003 | Heynen et al. |
| 6,512,952 B2 | 1/2003 | Stahmann et al. |
| 6,522,921 B2 | 2/2003 | Stahmann et al. |
| 6,522,923 B1 | 2/2003 | Turcott |
| 6,527,729 B1 | 3/2003 | Turcott |
| 6,553,258 B2 | 4/2003 | Stahmann et al. |
| 6,574,506 B2 | 6/2003 | Kramer et al. |
| 6,604,000 B2 | 8/2003 | Lu |
| 6,973,349 B2 | 12/2005 | Salo |
| 7,020,521 B1* | 3/2006 | Brewer et al. ............... 607/14 |
| 7,110,817 B2 | 9/2006 | Yu et al. |
| 2002/0002389 A1 | 1/2002 | Bradley et al. |
| 2002/0091415 A1* | 7/2002 | Lovett et al. ............... 607/14 |
| 2003/0014083 A1* | 1/2003 | Kupper ........................ 607/9 |
| 2003/0078624 A1 | 4/2003 | Carlson et al. |
| 2003/0105493 A1 | 6/2003 | Salo |
| 2003/0105496 A1 | 6/2003 | Yu et al. |
| 2003/0125774 A1 | 7/2003 | Salo |
| 2004/0122484 A1 | 6/2004 | Hatlestad et al. |
| 2005/0102001 A1 | 5/2005 | Maile et al. |
| 2005/0177195 A1 | 8/2005 | Salo |

FOREIGN PATENT DOCUMENTS

| | | |
|---|---|---|
| EP | 0474958 | 3/1992 |
| WO | WO-99/10042 | 3/1999 |
| WO | WO-01/76689 | 10/2001 |
| WO | WO-02/087694 | 11/2002 |

OTHER PUBLICATIONS

Ding, Jiang, et al., "Cardiac Pacing Using Adjustable Atrio-Ventricular Delays", U.S. Appl. No. 10/008,830, (Dec. 7, 2001), 1-42.

Ding, Jiang, et al., "Cardiac Pacing Using Adjustable Atrio-Ventricular Delays", U.S. Appl. No. 10/243,811, (Sep. 13, 2002), 1-39.

Ding, J., et al., "Cardiac Pacing Using Adjustable Atrio-Ventricular Delays", U.S. Appl. No. 11/049,181, filed Feb. 2, 2005, 35 pgs.

Kinderman, Michael, et al., "Optimizing the AV Delay in DDD Pacemaker Patients with High Degree AV Block: Mitral Valve Doppler Versus Impedance Cardiography", *PACE*, vol. 20, pp. 2453-2462, (Oct. 1997),2453-2462.

Lau, Chu-Pak, et al., "Chapter 7—Overview of Ideal Sensor Characteristics", *Clinical cardiac pacing / by Kenneth A Ellenbogen; G Neal Kay; Bruce L Wilkoff, Philadelphia : Saunders*,(1995),141-166.

Leonelli, Fabio M., et al., "Systolic and Diastolic Effects of Variable Atroventricular Delay and Patients with Complete Hear Block and Normal Ventricular Function", *Amer. J-Cardiology*, vol. 80, pp. 294-298, (Aug. 1, 1997),294-298.

Min, Mart, "Electrical Impedance and Cardiac Monitoring-Technology, Potential and Applications", *International Journal of Bioelectromagnetism*, 5(1), (2003),53-56.

Prinzen, Frits W., et al., "Mapping of regional myocardial strain and work during ventricular pacing: experimental study using magnetic resonance imaging tagging", *Journal of the American College of Cardiology*, 33(6), (May 1999), 1735-1742.

Reiter, Michael J., et al., "Electrophysiological Effects of Acute Dilatation in the Isolated Rabbit Hear", *Circulation*, vol. 96, No. 11, (Dec. 2, 1997),4050-4056.

Ritter, P., et al., "A Built-In System Based on the Peak Endocardial Acceleration (PEA) for AV-Delay Optimization in DDDR Pacing", *Pace*, 20(5) (Part II), (Abstract of Paper presented at EUROPACE '97),(May 1997),p. 1567.

Ritter, P., et al., "New Method for Determining the Optimal Atrio-Ventricular Delay in Patients Place in DDD Mode for Complete Atrio-Ventricular Block", *NASPE* abstract #237, p. 885, (1995),3.

Sgarbossa, Elena B., et al., "Chapter 17—Adverse Effects and Limitations of Rate-Adaptive Pacing", *New Perspectives in Cardiac Pacing*, 3 / by S. Serge Barold; Jacques Mugica, Mount Kisco, NY : Futura Pub. Co.,(1993),383-423.

Sheiban, I., et al., "Time course and determinants of left ventricular function recovery after primary angioplasty in patients with acute myocardial infarction", *J Am Coll Cardiol.*, 38(2), (Aug. 2001),464-71.

Suematsu, Yoshihiro, et al., "L-Arginine given after ischaemic preconditioning can enhance cardioprotection in isolated rat hearts", *European Journal of Cardio-thoracic Surgery*, 19 (2001),873-879.

Watanabe, Michiko, et al., "Developmental Remodeling and Shortening of Cardiac Outflow Tract Involves Myocyte Programmed Cell Death", *Development*, 125 (19), (1998),3809-3820.

Yu, Yinghong, et al., "Method and Apparatus for Optimizing Stroke Volume During DDD Resynchronization Therapy Using Adjustable Atrio-Ventricular Delays", U.S. Appl. No. 10/314,899, filed Dec. 9, 2002, 1-50.

Yu, Yinghong, et al., "Method and Apparatus for Optimizing Ventricular Synchrony During DDD Resynchronization Therapy Using Adjustable Atrio-Ventricular Delays", U.S. Appl. No. 10/314,910, filed Dec. 9, 2002, 1-50.

\* cited by examiner

DYNAMIC DEVICE THERAPY CONTROL FOR TREATING POST MYOCARDIAL INFARCTION PATIENTS

CROSS-REFERENCE TO RELATED APPLICATIONS

This application is related to co-pending, commonly assigned, U.S. patent application Ser. No. 09/962,852, "EVOKED RESPONSE SENSING FOR ISCHEMIA DETECTION," filed on Sep. 25, 2001, U.S. patent application Ser. No. 10/038,936, "METHOD AND APPARATUS FOR MEASURING LEFT VENTRICULAR PRESSURE," filed on Jan. 4, 2002, U.S. patent application Ser. No. 10/005,184, "METHOD AND APPARATUS FOR MINIMIZING POST-INFARCT VENTRICULAR REMODELING," filed on Dec. 5, 2001, U.S. patent application Ser. No. 10/314,910, "METHOD AND APPARATUS FOR OPTIMIZING VENTRICULAR SYNCHRONY DURING DDD RESYNCHRONIZATION THERAPY USING ADJUSTABLE ATRIO-VENTRICULAR DELAYS," filed on Dec. 9, 2002, U.S. patent application Ser. No. 10/314,899, "METHOD AND APPARATUS FOR OPTIMIZING STROKE VOLUME DURING DDD RESYNCHRONIZATION THERAPY USING ADJUSTABLE ATRIO-VENTRICULAR DELAYS," filed on Dec. 9, 2002, and U.S. patent application Ser. No. 10/703,175 "A DUAL-USE SENSOR FOR RATE RESPONSIVE PACING AND HEART SOUND MONITORING," filed on Nov. 6, 2003, which are hereby incorporated by reference in their entirety.

FIELD OF THE INVENTION

This document generally relates to cardiac rhythm management systems and particularly, but not by way of limitation, to such systems providing for cardiac pacing after myocardial infraction.

BACKGROUND

The heart is the center of a person's circulatory system. It includes an electro-mechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of the body to provide the organs with their metabolic needs for oxygen. The right portions of the heart, including RA and RV, draw deoxygenated blood from the body organs and pump it to the lungs where the blood gets oxygenated. These pumping functions are accomplished by cyclic contractions of the myocardium (heart muscles). Each cycle, known as the cardiac cycle, includes systole and diastole. Systole is the ejection phase of the cardiac cycle, during which the ventricles eject blood. Diastole is the relaxation phase of the cardiac cycle. The efficiency of the pumping functions, indicative whether the heart is normal and healthy, is indicated by measures of hemodynamic performance, such as parameters related to intracardiac blood pressures and cardiac output.

In a normal heart, the sinus node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply. As a physiological compensatory mechanism that acts to increase cardiac output in response to MI, the LV diastolic filling pressure increases as the pulmonary and venous blood volume increases. This increases the LV preload (stress on the LV wall before its contracts to eject blood), as measured by the left ventricular end diastolic pressure (LVEDP). One effect is the progressive change of the LV shape and size, a processes referred to as remodeling. Remodeling is initiated in response to a redistribution of cardiac stress and strain caused by the impairment of contractile function in the infarcted area as well as in nearby and/or interspersed viable myocardial tissue with lessened contractility due to the infarct. The remodeling starts with expansion of the infracted area and progresses to a chronic, global expansion in the size and change in the shape of the entire LV. Although the process is initiated by the compensatory mechanism that increases cardiac output, the remodeling ultimately leads to further deterioration and dysfunction of the myocardium. Consequently, post MI patients experience impaired hemodynamic performance and have a significantly increased risk of developing heart failure.

For these and other reasons, there is a need to control post MI remodeling and improve hemodynamic performance.

SUMMARY

A cardiac rhythm management system includes an implantable device executing a dynamic pacing algorithm after a myocardial infarction (MI) event. The dynamic pacing algorithm provides for improved hemodynamic performance when a person's metabolic need is high and post MI remodeling control when the person's metabolic need is low.

In one embodiment, an implantable medical device includes a sensing circuit, a pacing circuit, an activity sensor, and a pacing controller. The sensing circuit senses at least one electrogram. The pacing circuit delivers pacing pulses. The activity sensor senses an activity level. The pacing controller includes a dynamic pacing parameter controller, an MI detector, and a pacing algorithm selector. The dynamic pacing parameter controller receives an activation signal and, after the activation signal is received, controls one or more pacing parameters based on at least the activity level. The MI detector detects a signal indicative of an MI event. The pacing algorithm selector generates the activation signal after the signal indicative of the MI event is detected. In a further embodiment, a cardiac rhythm management system includes the implantable medical device and an external system communicating with the implantable medical device via telemetry. The external system includes a user input to receive commands controlling operations of the implanted medical device.

In one embodiment, a method for operating an implantable pacemaker includes detecting a signal indicative of an MI event and executing a dynamic pacing algorithm after the signal indicative of the MI event is detected. The execution of the dynamic pacing algorithm includes sensing an activity level, dynamically adjusting one or more pacing parameters based on at least the activity level, sensing at least one electrogram, and delivering pacing pulses.

In one embodiment, a cardiac pacing method includes sensing an activity level and comparing the activity level to a predetermined threshold. If the activity level exceeds the predetermined threshold, a cardiac resynchronization therapy (CRT) pacing algorithm is executed. If the activity level does not exceed the predetermined threshold, a remodeling control therapy (RCT) pacing algorithm is executed.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document. The drawing are for illustrative purposes only and not to scale nor anatomically accurate.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a method and system for delivering cardiac pacing therapy to post MI patients. Many post MI patients need both a therapy for improving hemodynamic performance and a therapy for controlling remodeling. The two therapies are delivered by executing a dynamic pacing algorithm, i.e., executing two pacing algorithms or applying two sets of pacing parameters alternately, depending on the patient's instant need and conditions. In this document, a "dynamic pacing algorithm" includes a comprehensive pacing algorithm that includes two or more pacing algorithms dynamically selected to be executed one at a time based on a command or signal, or a pacing algorithm that includes one or more pacing parameters dynamically adjusted based on a command or signal.

Figure 1:
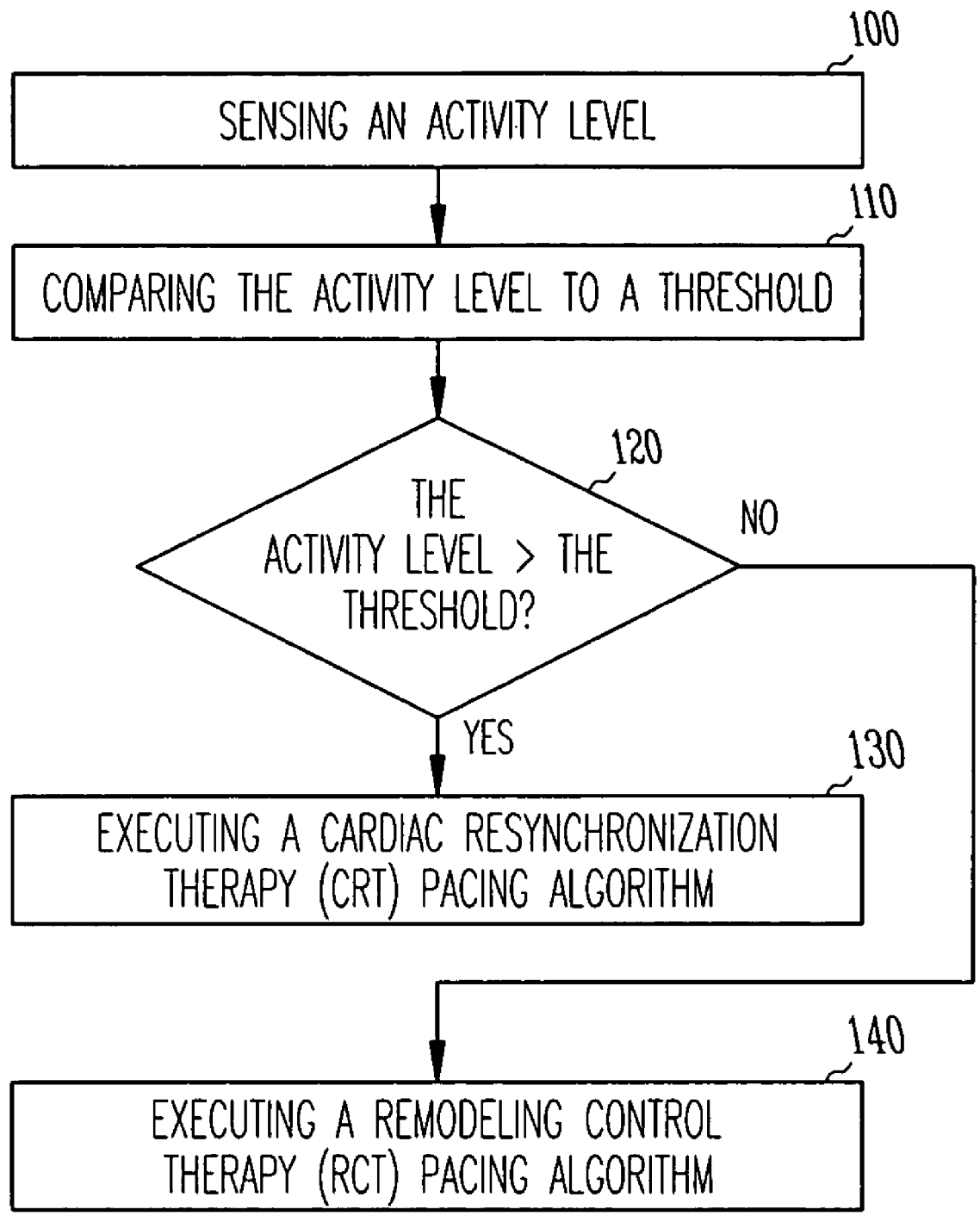
FIG. 1 is a flow chart illustrating an embodiment of a method for post MI cardiac pacing.

FIG. 1 is a flow chart illustrating an embodiment of such a post MI pacing method. In one embodiment, a cardiac resynchronization therapy (CRT) provides for an approximately optimal hemodynamic performance, and a remodeling control therapy (RCT) reduces the degree of post MI remodeling. In one embodiment, a CRT pacing algorithm is executed with one or more pacing parameters approximately optimized to maximize a measure of hemodynamic performance. Examples of determining such pacing parameters are discussed in U.S. patent application Ser. No. 10/314,910, "METHOD AND APPARATUS FOR OPTIMIZING VENTRICULAR SYNCHRONY DURING DDD RESYNCHRONIZATION THERAPY USING ADJUSTABLE ATRIO-VENTRICULAR DELAYS," and U.S. patent application Ser. No. 10/314,899, "METHOD AND APPARATUS FOR OPTIMIZING STROKE VOLUME DURING DDD RESYNCHRONIZATION THERAPY USING ADJUSTABLE ATRIO-VENTRICULAR DELAYS," both filed on Dec. 9, 2002, assigned to Cardiac Pacemakers, Inc., which are hereby incorporated by reference in their entirety. An RCT pacing algorithm is executed to reduce the degree of remodeling by redistributing the loading or stress on the LV wall. An example of post MI RCT is discussed in U.S. patent application Ser. No. 10/005,184, "METHOD AND APPARATUS FOR MINIMIZING POST-INFARCT VENTRICULAR REMODELING," filed on Dec. 5, 2001, assigned to Cardiac Pacemakers, Inc., which is hereby incorporated by reference in their entirety. Generally, the CRT and RCT cannot be delivered simultaneously because of conflicts between their effects. For example, pacing parameters that provide for most efficient remodeling control may not maximize hemodynamic performance. One therapy for treating post MI patients is to control the progress of post MI remodeling by reducing the preload in the infract region. Pacing pulses are delivered with a short atrioventricular (AV) delay to reduce the stress to this region prior to contraction. However, pacing with the short AV delay may result in reduced hemodynamic performance. For example, if the heart being paced with the short AV delay has a normal ventricular conduction (Purkinje) system, the pacing lowers measures of hemodynamic performance such as the degree of ventricular synchrony and the cardiac output. One consequent problem is that when a post MI patient becomes active, the pacing with the short AV delay may limit the cardiac output and hence, prevent the heart from pumping sufficient blood to meet the patient's metabolic need. One solution is to deliver the CRT and RCT on an alternating basis, depending on the metabolic need of the post MI patient, such that the pacing provides for optimal hemodynamic performance when the metabolic need is high, and post MI remodeling control when the metabolic need is low. In other words, a comprehensive therapy is delivered by executing a dynamic pacing algorithm, and that includes executing at least two specific pacing algorithms, such as the CRT and RCT pacing algorithms, on an alternating basis.

As illustrated in FIG. 1, an activity level is sensed at 100. The activity level is a measure of the intensity of the patient's gross physical activity, which in turn indicates the patient's metabolic need for oxygenated blood. In one embodiment, an acceleration signal is sensed as the activity level, such as by using an accelerometer implanted in the patient. In another embodiment, the patient's minute ventilation is sensed as the activity level, such as by using an impedance sensor implanted in the patient. In another embodiment, the heart rate of the patient is sensed as the activity level from an electrocardiogram or electrogram. The heart rate is usable as an indication of the activity level when it is an intrinsic heart rate, such as when the patient receives VDD mode pacing.

The activity level is compared to a predetermined threshold at 110. The threshold corresponds to an activity level above which a need to improve or maintain hemodynamic performance is indicated. The threshold is determined based on the patient's physiological condition, lifestyle, and other factors indicative of a need for improving hemodynamics by pacing. In one embodiment, the threshold is determined empirically based on statistical analysis of data from multiple patients. In one embodiment, the threshold is determined based on each individual patient's circumstances, such as physiological conditions and desirable lifestyle. In one embodiment, the threshold is adaptive and adjusted in response to changes the patient's physiological condition, lifestyle, and other factors.

If the activity level exceeds the predetermined threshold at 120, the CRT pacing algorithm is executed at 130. If the activity level does not exceed the predetermined threshold at 120, the RCT pacing algorithm is executed at 140. In one embodiment, the threshold corresponds to an activity level above which the patient is indicated as being exercising (or conducting a physical activity with the intensity comparable to that of exercising). The patient receives CRT when exercising and RCT when not exercising. In one embodiment, the threshold corresponds to an activity level below which the patient is indicated as being sleeping. The patient receives RCT while sleeping and CRT while being awake. In one embodiment, executing the CRT pacing algorithm includes selecting a set of pacing parameter values to approximately maximize a measure of hemodynamic performance, and executing the RCT pacing algorithm includes selecting another set of pacing parameter values providing for approximately optimal preload reduction in the infarcted area. Studies have shown that the two sets of pacing parameter values are significantly different. In one embodiment, the pacing parameters that are used but with distinct values for the CRT and RCT include pacing sites, AV delays, and/or interventricular delays. In one specific embodiment, the CRT pacing algorithm uses one or more AV delays that are significantly longer than those of the RCT pacing algorithm.

In one embodiment, the activity level is sensed and compared to the threshold continuously. In another embodiment, the activity level is sensed and compared to the threshold according to a predetermined schedule. In another embodiment, the activity level is sensed and compared to the threshold on a periodical basis. The pacing algorithm being executed changes when the outcome of the comparison changes.

It is to be understood that the CRT and RCT are used to illustrate the method by way of example, but not by way of limitation. The method discussed herein using the CRT and RCT as examples applies to a pacing therapy with two or more pacing algorithms dynamically selected and executed to serve a plurality of therapy objectives. In general, the method discussed above, using the CRT, RCT, and activity level as examples, is generally applicable to a comprehensive treatment of a patient with any abnormal condition, where the comprehensive treatment includes a first therapy, a second therapy, and a signal or parameter indicating when the first therapy is to be delivered and when the second therapy is to be delivered.

Figure 2:
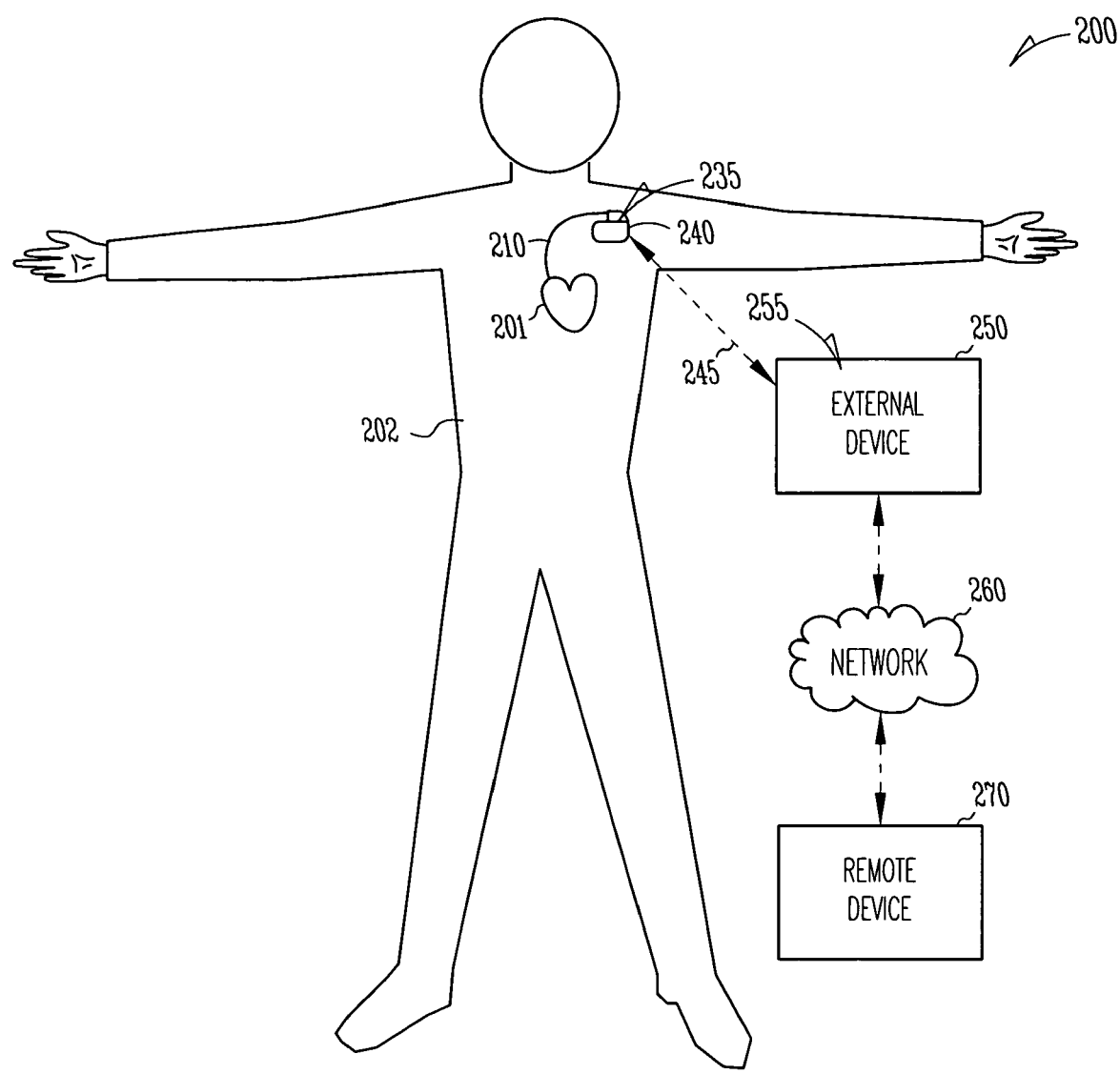
FIG. 2 is an illustration of an embodiment of a cardiac rhythm management (CRM) system and portions of an environment in which it is used.

FIG. 2 is a schematic/block diagram illustrating one embodiment of portions of a CRM system 200 and portions of the environment in which it is used. CRM system 200 includes a cardiac pacing system to perform the method discussed above with reference to FIG. 1. In one embodiment, CRM system 200 includes an implantable system 235, an external system 255, and a telemetry link 245 providing for bidirectional communication between implantable system 235 and external system 255. Implantable system 235 includes an implantable device 240 and an implantable lead system 210. Implantable device 240 is implanted within a body 202 and electrically connected to a heart 201 via lead system 210. Implantable device 240 is an implantable pacemaker or any implantable medical device with a pacemaker circuit, such as a pacemaker-defibrillator. In one embodiment, the implantable pacemaker provides for the CRT pacing and RCT pacing. In one embodiment, lead system 210 includes an atrial pacing lead having one or more electrodes placed in the right atrium, and one ventricular pacing lead having one or more electrodes placed in a ventricle. In another embodiment, multiple ventricular sites are paced, and lead system 210 includes multiple ventricular pacing leads each having one or more electrodes to be placed in the LV and/or the RV.

In one embodiment, external system 255 is a patient management system including an external device 250 in proximity of implantable device 240, a remote device 270 in a relatively distant location, and a telecommunication network 260 linking external device 250 and remote device 270. The patient management system allows access to implantable system 235 from a remote location, for purposes such as monitoring patient status and adjusting therapies without the need of the patient's presence. In another embodiment, external system 255 includes a programmer that provides for patient monitoring, device monitoring, and device programming.

In one embodiment, telemetry link 245 is an inductive telemetry link. In another embodiment, telemetry link 245 is a far-field radio-frequency telemetry link. In one embodiment, telemetry link 245 provides for data transmission from implantable device 240 to external system 255. This may include, for example, transmitting real-time physiological data acquired by implantable device 240, extracting physiological data acquired by and stored in implantable device 240, extracting therapy history data stored in implantable device 240, and extracting data indicating an operational status of implantable device 240 (e.g., battery status and lead impedance). In a further embodiment, telemetry link 245 provides for data transmission from external system 255 to implantable device 240. This may include, for example, programming implantable device 240 to acquire physiological data, programming implantable device 240 to perform at least one self-diagnostic test (such as for a device operational status), and programming implantable device 240 to deliver at least one therapy, including selecting pacing algorithms and programming therapy parameters.

Figure 3:
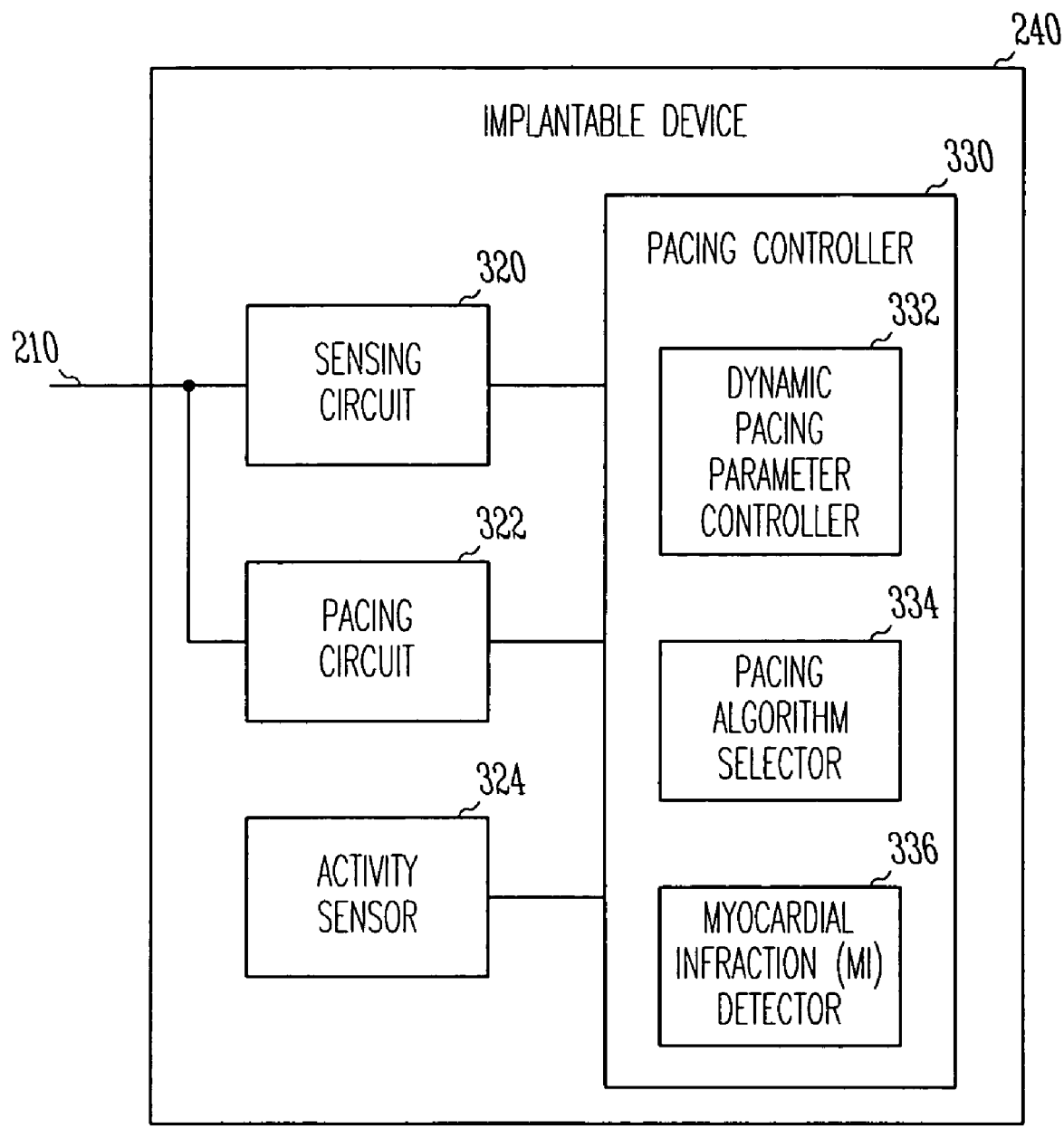
FIG. 3 is a block diagram showing one embodiment of portions of the circuit of an implantable device of the CRM system.

FIG. 3 is a block diagram showing one embodiment of portions the circuit of implantable device 240. Implantable device 240 includes a sensing circuit 320, a pacing circuit 322, an activity sensor 324, and a pacing controller 330. In one embodiment, implantable device 240 includes a hermetically sealed metal can to house at least portions of the electronics.

Sensing circuit 320 and pacing circuit 322 are electrically connected to heart 201 through lead system 210. Lead system 210 includes one or more leads having electrodes placed in intracardiac sites. Sensing circuit 320 senses one or more electrograms each from one interested region in heart 201. Pacing circuit 322 includes pacing channels each individually controllable to deliver pacing pulses to one targeted region in heart 201. In one embodiment, sensing circuit 320 senses electrograms from an atrial region and a ventricular region. Pacing circuit 322 delivers pacing pulses to at least the ventricular site with a programmable AV delay. In one embodiment, sensing circuit 320 senses electrograms from an atrial region and a plurality of ventricular regions. Pacing circuit 322 delivers pacing pulses to one or more of the ventricular regions, with individually programmable AV delays. Each region corresponds to at least one electrode site. When pacing pulses are delivered to two or more ventricular regions, the timing of the delivery is controlled with either individually controlled AV delays or with one AV delay and one or more interventricular delays. For example, if pacing pulses are delivered to an RV site and an LV site, in one embodiment, RV pacing pulses are each delivered with an AV delay for RV, $AVD_{RV}$, and LV pacing pulses are each delivered with an AV delay for LV, $AVD_{LV}$. In an alternative embodiment, RV pacing pulses are each delivered with an AV delay for RV, $AVD_{RV}$, and LV pacing pulses are each delivered with an interventricular delay between RV and LV, $IVD_{LV-RV}$, where $IVD_{LV-RV}=AVD_{LV}-AVD_{RV}$.

Activity sensor 324 senses an activity level being a measure of the intensity of the patient's gross physical activities. In one embodiment, activity sensor 324 includes a heart rate monitor to detect a heart rate indicative of the activity level. In one specific embodiment, the heart rate monitor includes an event detector to detect ventricular contractions from a ventricular electrogram, measures the time interval between two consecutively detected ventricular contractions, and calculates the heart rate based on the time interval. In another specific embodiment, the heart rate monitor includes an event detector to detect atrial contractions from an atrial electrogram, measures the time interval between two consecutively detected atrial contractions, and calculates the heart rate based on the time interval. In one embodiment, activity sensor 324 includes an accelerometer to sense an acceleration signal indicative of the activity level. In one specific embodiment, the accelerometer is housed within the hermetically sealed can. In another specific embodiment, the accelerometer is incorporated into a lead of lead system 210, so as to be placed near or within the heart. In one embodiment, activity sensor 324 includes a respiratory sensor to sense a signal indicative of the patient's minute ventilation. In one specific embodiment, the respiratory sensor is an impedance sensor sensing thoracic impedance indicative of the pulmonary volume.

Pacing controller 330 controls the delivery of pacing pulses by executing a pacing algorithm and includes a dynamic pacing parameter controller 332, a pacing algorithm selector 334, and a myocardial infarction detector (MI detector) 336. In one embodiment, pacing controller 330 controls whether and when a pacing pulse is delivered from each of the pacing channels of pacing circuit 322. This includes control of pacing sites (whether to deliver a pacing pulse to an electrode site), control of AV delays (when to deliver a ventricular pacing pulse after a sensed or paced atrial event), and control of interventricular delays (when to deliver a pacing pulse to one ventricular site after a sensed or paced event in another ventricular site).

Dynamic pacing parameter controller 332 supports the execution of a dynamic pacing algorithm by dynamically adjusting one or more pacing parameters in response to a changing activity level. In one embodiment, dynamic pacing parameter controller 332 includes an AV delay adjuster to dynamically adjusting at least one AV delay based on at least the activity level. In one specific embodiment, the AV delay adjuster includes an AV delay selector to dynamically select a value for the at least one AV delay from a plurality of preset AV delay values based on at least the activity level. When the dynamic pacing algorithm includes pacing multiple ventricular sites, in one embodiment, dynamic pacing parameter controller 332 includes the AV delay adjuster adjusts multiple AV delays. In an alternative embodiment, dynamic pacing parameter controller 332 includes the AV delay adjuster to adjust one AV delay and an interventricular delay adjuster to adjust at least one interventricular delay. In one specific embodiment, the interventricular delay adjuster includes an interventricular delay selector to dynamically select a value for the at least one interventricular delay from a plurality of preset interventricular delay values based on at least the activity level. In one embodiment, dynamic pacing parameter controller 332 further includes a pacing channel selector to dynamically select one or more pacing channels from a plurality of preset pacing channels based on at least the activity level. In one embodiment, dynamic pacing parameter controller 332 includes a parameter receiver to receive values for the one or more pacing parameters. In one specific embodiment, the parameter receiver receives the preset AV delays, interventricular delays, and/or pacing channels as they are programmed into implantable device 240. Dynamic pacing parameter controller 332 includes an activity level comparator to compare the sensed activity level to a threshold level indicative of a need for the pacing parameter adjustment. In one embodiment, the activity level comparator compares the sensed activity level to one or more predetermined activity level thresholds to produce two or more activity level ranges. Each activity level range corresponds to a predetermined set of one or more pacing parameter values. In one embodiment, such as in the example of the alternating execution of the CRT and RCT pacing algorithms, each predetermined set of one or more pacing parameter values corresponds to one of the pacing algorithms being part of a dynamic pacing algorithm. In this embodiment, dynamic pacing parameter controller 332 effectively switches pacing algorithms by adjusting pacing parameters. In one specific embodiment, dynamic pacing parameter controller 332 changes the pacing algorithm being executed from the CRT pacing algorithm to the RCT pacing algorithm by shortening one or more AV delays, adjusting one or more interventricular delays, and/or reselecting one or more pacing channels.

Pacing algorithm selector 334 selects one or more pacing algorithms to be executed by pacing controller 330 in response to an algorithm selection signal. When the algorithm selection signal calls for a dynamic pacing algorithm which requires dynamic pacing parameter adjustments during the execution, pacing algorithm selector 334 generates an activation signal to activate dynamic pacing parameter controller 332. In one embodiment, pacing algorithm selector 334 includes a timer to time a predetermined time period starting with the MI event and generates the activation signal after the predetermined period expires. Because post MI remodeling progresses in stages, a post MI RCT pacing is timed to start and/or be adjusted at appropriate times.

MI detector 336 detects a signal indicative of an MI event and produces the algorithm selection signal calling for the dynamic pacing algorithm in response to a detection. Thus, pacing algorithm selector 334 generates the activation signal to activate dynamic pacing parameter controller 332 after the signal indicative of the MI event is detected. In one embodiment, MI detector 336 includes a command receiver to receive an external activation command sent to implantable device 240 as the signal indicative of the MI event. In one specific embodiment, the external activation command is issued by a physician or other caregiver in response to the diagnosis of MI. This embodiment is suitable for use, for example, when implantable device 240 is implanted into a patient having experienced MI. In one embodiment, MI detector 336 detects the signal indicative of the MI event from the physiological signals sensed by implantable device 240. In one embodiment, MI detector 336 includes an ischemia detector housed in implantable device 240. In one specific embodiment, MI detector 336 includes an electrogram-based ischemia detector to detect an ischemia as the signal indicative of the MI event. One example of the electrogram-based ischemia detector is discussed in U.S. patent application Ser. No. 09/962,852, entitled "EVOKED RESPONSE SENSING FOR ISCHEMIA DETECTION," filed on Sep. 25, 2001, assigned to Cardiac Pacemakers, Inc., which is incorporated herein by reference in its entirety. In another specific embodiment, MI detector 336 includes an impedance-based ischemia detector. The ischemia detector includes an electrical impedance based sensor using a low carrier frequency (e.g. 100 Hz) and an ischemia analyzer running an automatic ischemia detection algorithm to detect an ischemic condition from the electrical impedance signal. Tissue electrical impedance has been shown to increase significantly during ischemia, as discussed in Min, et al. *International Journal of Bioelectromagnetism*, 5(1):53–56 (2003). The ischemia detector senses low frequency electrical impedance signal between electrodes interposed in the heart, and detects the ischemia as abrupt changes in impedance (such as abrupt increases in value). In another embodiment, the ischemia detector includes a local heart motion based sensor utilizing an accelerometer located within a lead body positioned on or in the heart and an ischemia analyzer running an automatic ischemia detection algorithm to detect an ischemic condition from the acceleration signal. The ischemia detector detects ischemia as an abrupt decrease in the amplitude of local cardiac accelerations. Detecting the signal indicative of the MI event by implantable device 240 is suitable, for example, when the implantable device is implanted into a patient having not experienced MI but is at significant risk of a future MI event.

Figure 4:
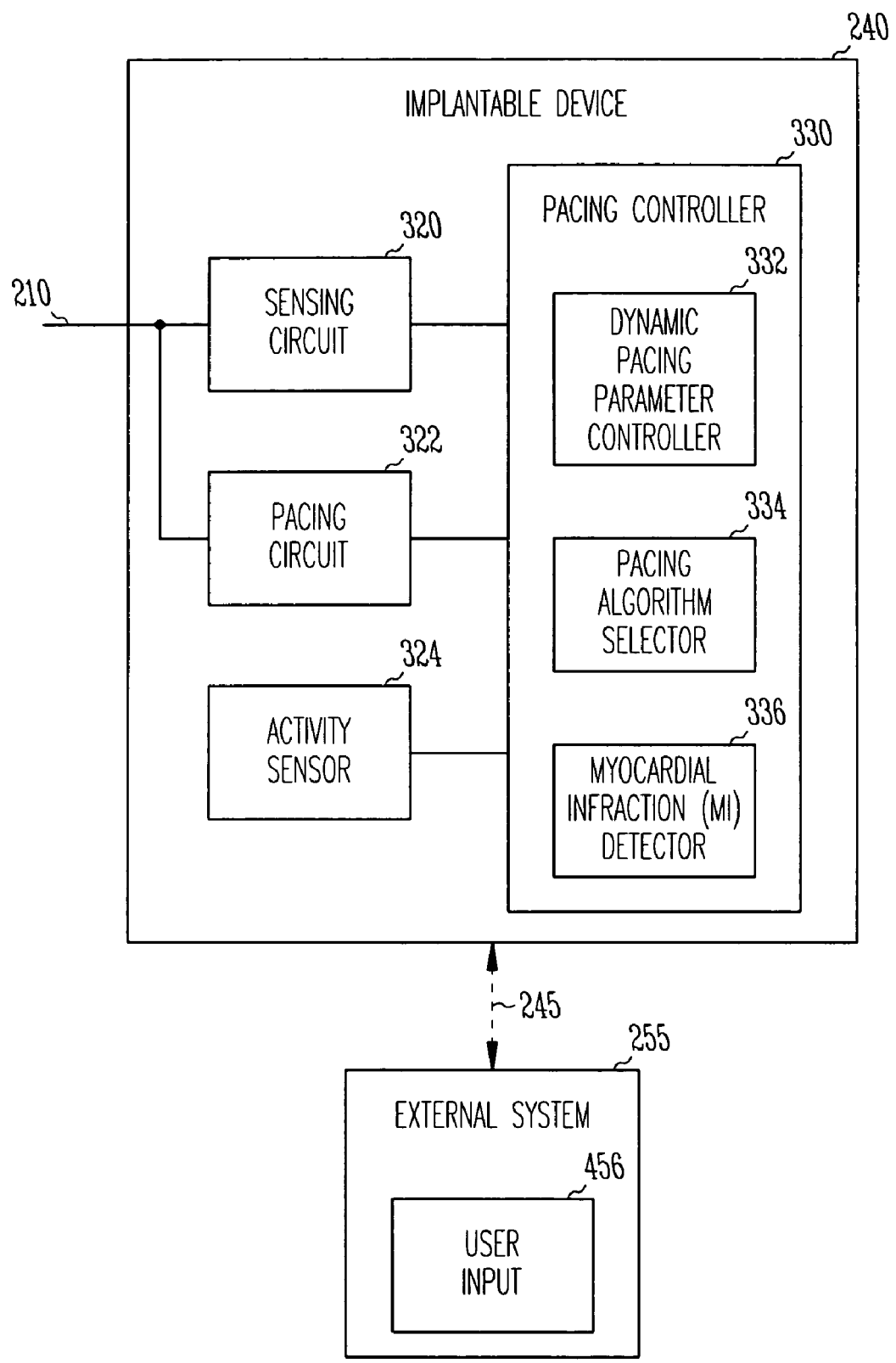
FIG. 4 is a block diagram showing one embodiment of portions of the circuit of the implantable device and portions of the circuit of an external system of the CRM system.

FIG. 4 is a block diagram showing one embodiment of portions of the circuit of implantable device 240 and portions of the circuit of external system 255. Implantable device 240 communicates with external system 255 via telemetry link 245.

External system 255 includes a user input 456 to receive commands from the physician or other caregiver controlling operations of implantable device 240. User input 456 receives a user activation command and issues the external activation command, which is transmitted to implantable device 240 via telemetry 245. In one embodiment, user input 456 also receives values for the pacing parameters such as the preset AV delays, interventricular delays, and pacing channels. In one embodiment, user input 456 includes an on/off selector allowing an entry of the user activation command by an on-selection. In another embodiment, user input 456 includes toggle switch allowing an entry of the user activation command by switching to the on-position. In one embodiment, user input 456 includes numerical entry fields to receive values for the pacing parameters, such as the preset AV delay values, the preset interventricular delay values, and the preset pacing channels. The pacing parameter values are programmed into pacing controller 330 of implantable device 240 via telemetry.

In one embodiment, external system 255 includes a programmer with user input 456. In another embodiment, external system 255 is a patient management system including external device 250, network 260, and remote device 270. In one embodiment, external device 250 includes user input 456 to allow the physician or other caregiver to enter the external activate command and/or the preset pacing parameter values in the presence of the patient. In one embodiment, remote device 270 includes user input 456 to allow the physician or other caregiver to enter the external activate command and/or the preset pacing parameter values from a remote location, eliminating the need of directly seeing the patient before delivering a new therapy.

Figure 5:
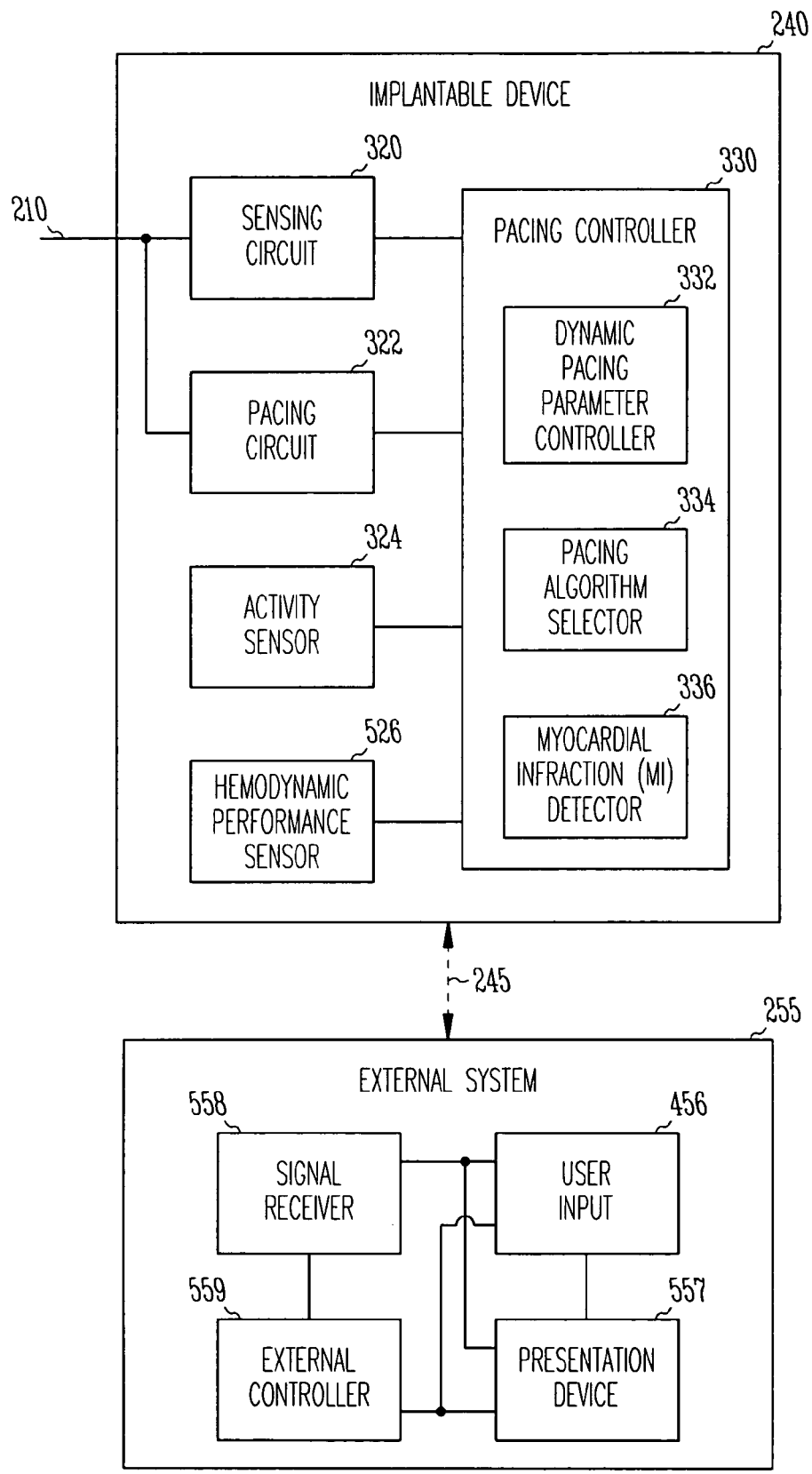
FIG. 5 is a block diagram showing one further embodiment of portions of the circuit of the implantable device and portions of the circuit of the external system of the CRM system.

FIG. 5 is a block diagram showing one further embodiment of portions of the circuit of implantable device 240 and portions of the circuit of external system 255. In this embodiment, implantable device 240 further includes a hemodynamic performance sensor 526 to sense a signal indicative of hemodynamic performance. In one embodiment, pacing controller 330 includes a signal analyzer to receive and analyze the signal indicative of hemodynamic performance. Pacing algorithm selector 334 determines whether to activate or deactivate dynamic pacing parameter controller 332 based on the signal indicative of hemodynamic performance. For example, pacing algorithm selector 334 stops executing a dynamic pacing algorithm that includes the CRT and RCT pacing algorithms, and starts executing a CRT-only pacing algorithm, when a measure of hemodynamic performance reaches an intolerable level while executing the RCT pacing algorithm. In another embodiment, dynamic pacing parameter controller 332 adjusts the one or more pacing parameters based on the activity level and the signal indicative of hemodynamic performance, so as to ensure that the parameter adjustment does not cause intolerable hemodynamic performance. In another embodiment, pacing controller 330 uses the signal indicative of hemodynamic performance to dynamically optimizing pacing parameters for the CRT.

In one embodiment, hemodynamic performance sensor 526 includes a minute ventilation sensor. In one specific embodiment, in which activity sensor 324 includes a minute ventilation sensor, the minute ventilation sensor is used as both activity sensor 324 and hemodynamic performance sensor 526.

In one embodiment, hemodynamic performance sensor 526 includes an acoustic sensor to sense heart sounds. In one specific embodiment, the signal analyzer includes a heart sound analyzer to detect first heart sounds (S1) and measure an S1 amplitude and/or duration. In another specific embodiment, the signal analyzer includes a heart sound analyzer to detect third heart sounds (Ss) and measure an S3 amplitude.

In one embodiment, the acoustic sensor includes an accelerometer. In one specific embodiment, the acoustic sensor and activity sensor are implemented as one single accelerometer, for example, as discussed in U.S. patent application Ser. No. 10/703,175, "A DUAL-USE SENSOR FOR RATE RESPONSIVE PACING AND HEART SOUND MONITORING," filed on Nov. 6, 2003, assigned to Cardiac Pacemakers, Inc., which is hereby incorporated by reference in their entirety.

In one embodiment, hemodynamic performance sensor 526 includes a pressure sensor to sense a signal indicative of an LV pressure. The signal analyzer includes a pressure analyzer to calculate the maximum positive derivative of the LV pressure, denoted by the term "LV+dp/dt." LV+dp/dt is a measure of LV synchrony, also known LV contractility. The LV pressure is measured directly or indirectly by sensing another pressure having a known or predictable relationship with the LV pressure. Examples of pressures having known or predictable relationships with the LV pressure during all or a portion of the cardiac cycle include an LA pressure and a coronary vein pressure. One specific example of measuring the LV pressure using a coronary vein pressure sensor is discussed in U.S. patent application Ser. No. 10/038,936, "METHOD AND APPARATUS FOR MEASURING LEFT VENTRICULAR PRESSURE," filed on Jan. 4, 2002, assigned to Cardiac Pacemakers, Inc., which is hereby incorporated by reference in its entirety. In one embodiment, such as a CRT, one or more pacing parameters are optimized for a maximum LV+dp/dt.

In one embodiment, hemodynamic performance sensor 526 includes a stroke volume sensor to sense a signal indicative of a stroke volume. An example of stroke volume sensing is discussed in U.S. Pat. No. 4,686,987, "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND," assigned to Cardiac Pacemakers, Inc., which is incorporated herein by reference in their entirety. In one embodiment, such as a CRT, one or more pacing parameters are optimized for a maximum stroke volume.

In the embodiment of FIG. 5, external system 255 further includes a signal receiver 558, a presentation device 557, and an external controller 559. Signal receiver 558 receives signals acquired by implantable device 240, including one or more electrograms, the activity level, and the signal indicative of hemodynamic performance. Presentation device 557 presents the received signals to the physician or other caregiver. In one embodiment, the physician or other caregiver responds by entering the user activation command and/or the pacing parameter values through user input 456. In one embodiment, external controller 559 analyzes the received signals and automatically issues the external activation command when deemed necessary.

In one embodiment, external system 255 includes a programmer with user input 456, signal receiver 558, presentation device 557, and external controller 559. In another embodiment, external system 255 is a patient management system including external device 250, network 260, and remote device 270. The physical distribution of user input 456, signal receiver 558, presentation device 557, and external controller 559 in external system 255 depends on overall considerations of factors such as need, convenience of use, and feasibility of implementation.

Figure 6:
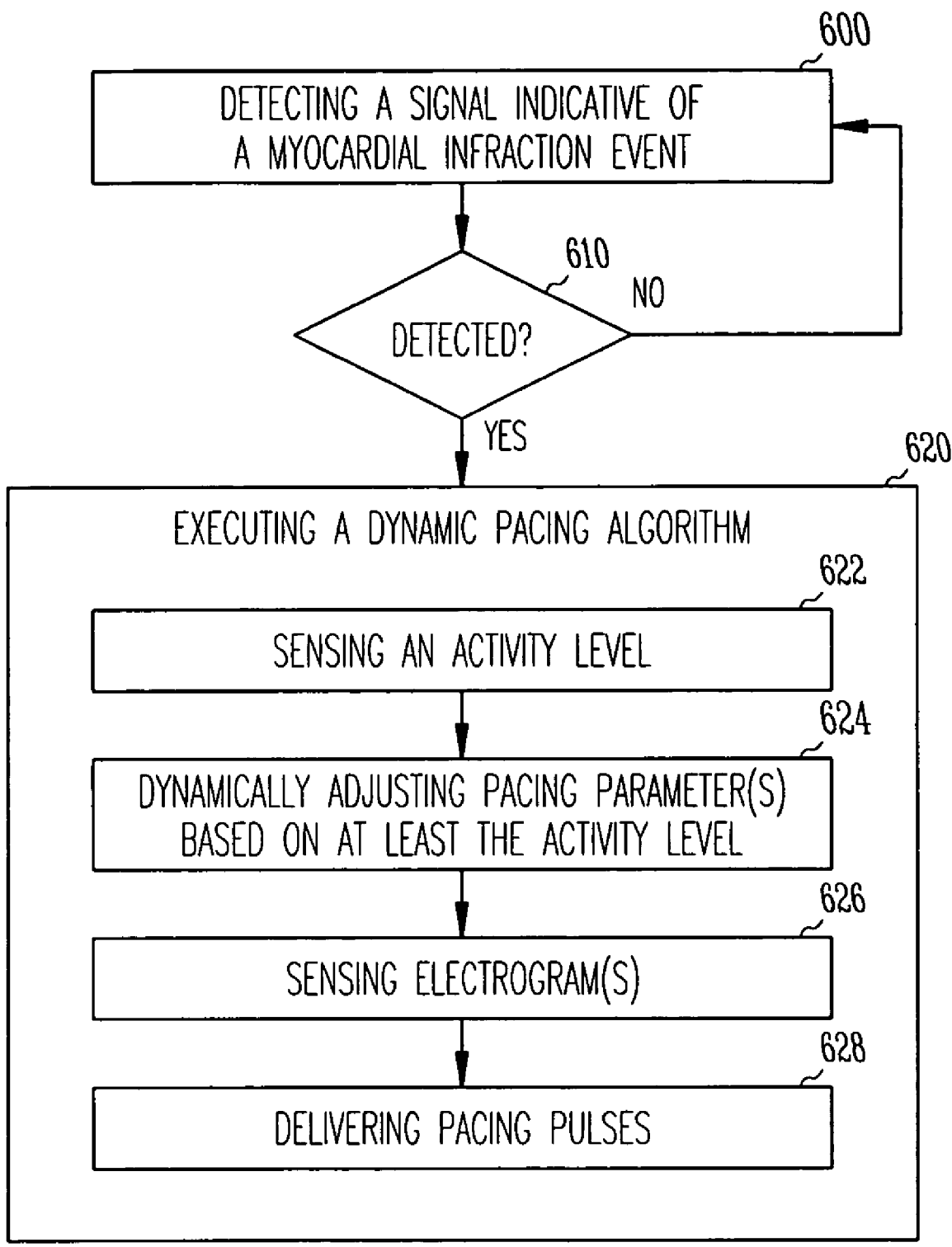
FIG. 6 is a flow chart illustrating an embodiment of a method for operating an implantable medical device to deliver post MI cardiac pacing.

FIG. 6 is a flow chart illustrating an embodiment of a method for operating an implantable medical device to deliver post MI cardiac pacing. In one embodiment, the method is performed by using CRM system 200, which includes implantable device 240.

A signal indicative of an MI event is being detected at 600. In one embodiment, detecting the signal indicative of the MI event includes receiving an external activation command issued in response to a diagnosis of MI. The external activation signal is considered as the signal indicative of the MI event. In another embodiment, the signal indicative of the MI event is a signal indicative of ischemia detected from a physiological signal such as an electrogram, an impedance signal, or a cardiac wall motion signal using one or more implantable ischemia detectors, such as those discussed above with reference to FIG. 3.

If the signal indicative of the MI event is detected at 610, a dynamic pacing algorithm is executed at 620. In one embodiment, a predetermined time period starts when the signal indicative of the MI event is detected, and the execution of the dynamic pacing algorithm starts upon the expiration of the predetermined time period.

The pacing algorithm execution at 620 includes sensing an activity level at 622, dynamically adjusting one or more pacing parameters based on at least the activity level at 624, sensing at least one electrogram at 626, and delivering pacing pulses at 628. The activity level is a measure of the intensity of a post MI patient's physical activities, such as the patient's heart rate, acceleration signal acquired by an accelerometer implanted in the patient, and the patient's minute ventilation. In one embodiment, the activity level is compared one or more predetermined thresholds, and the one or more pacing parameters are adjusted based on the outcome of the comparison. In one embodiment, the one or more pacing parameters to be dynamically adjusted include at least one AV delay. In another embodiment, the one or more pacing parameters to be dynamically adjusted include at least one AV delay and one interventricular delay. In one specific embodiment, the AV delay and/or interventricular delay are adjusted by selecting from a plurality of preset AV delay and/or interventricular delay values based on at least the activity level. In one embodiment, the one or more pacing parameters to be dynamically adjusted include pacing channels. One or more pacing channels are selected from a set of cardiac sites where pacing electrodes are placed.

In one embodiment, a signal indicative of the patient's hemodynamic performance is sensed. In one embodiment, the signal indicative of the patient's hemodynamic performance is used to determine the one or more pacing parameters such as the AV delay, interventricular delay, and pacing channels. In one embodiment, the signal indicative of the patient's hemodynamic performance is used to determine whether the dynamic pacing algorithm should be executed. In one further embodiment, the signal indicative of the patient's hemodynamic performance is used to determine whether the execution should be interrupted or stopped. Examples of the signal indicative of the hemodynamic performance include the patient's minute ventilation, S1 amplitude and duration, S3 amplitude, LV+dp/dt, and stroke volume.

It is to be understood that the above detailed description is intended to be illustrative, and not restrictive. For example, the method of automatically and selectively executing two or more therapy algorithms can be applied to treat non-cardiac conditions, and not necessarily by using an implantable device. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. An implantable pacemaker comprising:
   a sensing circuit to sense at least one electrogram;
   a pacing circuit to deliver pacing pulses;
   an activity sensor to sense an activity level; and
   a pacing controller coupled to the sensing circuit, the pacing circuit, and the activity sensor, the pacing controller including:
      a dynamic pacing parameter controller adapted to be activated by an activation signal and adapted to dynamically adjust one or more pacing parameters based on at least the activity level after being activated;
      a myocardial infarction detector to detect a signal indicative of a myocardial infarction event; and
   a pacing algorithm selector adapted to generate the activation signal after the signal indicative of the myocardial infarction event is detected.

2. The implantable pacemaker of claim 1, wherein the activity sensor comprises a heart rate monitor to detect a heart rate indicative of the activity level.

3. The implantable pacemaker of claim 1, wherein the activity sensor comprises an accelerometer to sense an acceleration indicative of the activity level.

4. The implantable pacemaker of claim 1, wherein the activity sensor comprises a minute ventilation sensor to sense a signal indicative of a minute ventilation.

5. The implantable pacemaker of claim 4, wherein the minute ventilation sensor comprises an impedance sensor.

6. The implantable pacemaker of claim 1, wherein the dynamic pacing parameter controller comprises an atrioventricular (AV) delay adjuster adapted to dynamically adjusting at least one AV delay based on at least the activity level.

7. The implantable pacemaker of claim 6, wherein the AV delay adjuster comprises an AV delay selector to dynamically select a value for the at least one AV delay from a plurality of predetermined AV delay values based on at least the activity level.

8. The implantable pacemaker of claim 6, wherein the dynamic pacing parameter controller further comprises an interventricular delay adjuster adapted to dynamically adjusting at least one interventicular delay based on at least the activity level.

9. The implantable pacemaker of claim 8, wherein the interventricular delay adjuster comprises an interventricular delay selector to dynamically select a value for the at least one interventricular delay from a plurality of predetermined interventricular delay values based on at least the activity level.

10. The implantable pacemaker of claim 6, wherein the pacing circuit comprises a plurality of pacing channels to deliver the pacing pulses to a plurality of cardiac sites, and the dynamic pacing parameter controller comprises a pacing channel selector adapted to dynamically select a predetermined set of one or more pacing channels from the plurality of pacing channels based on at least the activity level.

11. The implantable pacemaker of claim 10, further comprising an activity level comparator to compare the activity level to one or more predetermined activity level thresholds, wherein the dynamic pacing parameter controller is adapted to control one or more pacing parameters based on at least the result of the comparison.

12. The implantable pacemaker of claim 11, wherein the pacing algorithm selector comprises a timer to time a predetermined period starting when the signal indicative of the myocardial infarction event is detected and activate the dynamic pacing parameter controller after the predetermined period expires.

13. The implantable pacemaker of claim 1, wherein the myocardial infarction detector comprises a command receiver to receive an external activation command issued in response to the myocardial infarction event, the external activation command being the signal indicative of the myocardial infarction event.

14. The implantable pacemaker of claim 13, wherein the dynamic pacing parameter controller further comprises a parameter receiver to receive values for the one or more pacing parameters.

15. The implantable pacemaker of claim 1, wherein the myocardial infarction detector comprises an ischemia detector.

16. The implantable pacemaker of claim 15, wherein the ischemia detector comprises an electrogram-based ischemia detector.

17. The implantable pacemaker of claim 15, wherein the ischemia detector comprises an impedance sensor.

18. The implantable pacemaker of claim 15, wherein the ischemia detector comprises an accelerometer sensing cardiac wall motion.

19. The implantable pacemaker of claim 1, further comprising a hemodynamic performance sensor to sense a signal indicative of hemodynamic performance.

20. The implantable pacemaker of claim 19, wherein the pacing controller comprises a signal analyzer to receive the signal indicative of hemodynamic performance, and the pacing algorithm selector determines whether to activate or deactivate the dynamic pacing parameter controller based on the signal indicative of hemodynamic performance.

21. The implantable pacemaker of claim 20, wherein the hemodynamic performance sensor comprises an impedance sensor sensing a signal indicative of minute ventilation.

22. The implantable pacemaker of claim 20, wherein the hemodynamic performance sensor comprises an acoustic sensor to sense heart sounds and a heart sound analyzer to detect first heart sounds (S1) and measure an S1 duration.

23. The implantable pacemaker of claim 20, wherein the hemodynamic performance sensor comprises a pressure sensor to sense a signal indicative of a left ventricular pressure and a pressure analyzer to calculate an maximum positive derivative of the left ventricular pressure, LV+dp/dt.

24. The implantable pacemaker of claim 20, wherein the hemodynamic performance sensor comprises a stroke volume sensor to sense a signal indicative of stroke volume.

25. A cardiac rhythm management system, comprising:
   an implantable medical device including:
      a sensing circuit to sense at least one electrogram;
      a pacing circuit to deliver pacing pulses;
      an activity sensor to sense an activity level; and
      a pacing controller coupled to the sensing circuit, the pacing circuit, and the activity sensor, the pacing controller including:
         a dynamic pacing parameter controller adapted to be activated by an activation signal and adapted to dynamically adjust one or more pacing parameters based on at least the activity level after being activated;
         a myocardial infarction detector to detect a signal indicative of a myocardial infarction event; and
         a pacing algorithm selector adapted to generate the activation signal after the signal indicative of the myocardial infarction event is detected; and an external system communicatively coupled to the implantable medical device via telemetry, the external system including a user input to receive commands controlling operations of the implanted medical device.

26. The cardiac rhythm management system of claim 25, wherein the myocardial infarction detector comprises a command receiver to receive an external activation command as the signal indicative of the myocardial infarction event, and the user input is adapted to receive a user activation command and issue the external activation command in response to the user activation command.

27. The cardiac rhythm management system of claim 26, wherein the user input comprises an on/off selector allowing an entry of the user activation command by an on-selection.

28. The cardiac rhythm management system of claim 26, wherein the dynamic pacing parameter controller further comprises a parameter receiver to receive values for the one or more pacing parameters, and the user input comprises parameter entry fields to receive one or more values for the one or more pacing parameters.

29. The cardiac rhythm management system of claim 26, wherein the implantable medical device further comprises a hemodynamic performance sensor to sense a signal indicative of hemodynamic performance.

30. The cardiac rhythm management system of claim 29, wherein the hemodynamic performance sensor comprises the activity sensor.

31. The cardiac rhythm management system of claim 29, wherein the external system comprises a signal receiver to receive one or more of the at least one electrogram, the activity level, and the signal indicative of hemodynamic performance.

32. The cardiac rhythm management system of claim 31, wherein the external system comprises a presentation device to present the received one or more of the at least one electrogram, the signal indicative of hemodynamic performance.

33. The cardiac rhythm management system of claim 31, wherein the external system comprises an external controller to issue the external activation command based on the received one or more of the at least one electrogram, the signal indicative of a measure of hemodynamic performance.

34. The cardiac rhythm management system of claim 31, wherein the external system comprises a programmer.

35. The cardiac rhythm management system of claim 31, wherein the external system comprises:
an external device coupled to the implantable medical device via telemetry;
a network coupled to the external device; and
a remote device coupled to the network.

36. The cardiac rhythm management system of claim 35, wherein the remote device comprises a presentation device and the user input.

37. A method for operating an implantable pacemaker, comprising:
detecting a signal indicative of a myocardial infarction event; and
executing a dynamic pacing algorithm after the signal indicative of the myocardial infarction event is detected, the executing including:
sensing an activity level;
dynamically adjusting one or more pacing parameters based on at least the activity level;
sensing at least one electrogram; and
delivering pacing pulses.

38. The method of claim 37, wherein sensing the activity level comprises detecting heart rate.

39. The method of claim 37, wherein sensing the activity level comprises sensing an acceleration signal.

40. The method of claim 37, wherein sensing the activity level comprises sensing a signal indicative of a minute ventilation.

41. The method of claim 37, wherein dynamically adjusting the one or more pacing parameters comprises dynamically adjusting at least one AV delay based on at least the activity level.

42. The method of claim 41, wherein dynamically adjusting the at least one AV delay comprises dynamically selecting a value for the at least one AV delay from a plurality of predetermined AV delay values based on at least the activity level.

43. The method of claim 41, wherein dynamically adjusting the one or more pacing parameters further comprises dynamically adjusting at least one interventricular delay based on at least the activity level.

44. The method of claim 43, wherein dynamically adjusting the at least one interventricular delay comprises dynamically selecting a value for the at least one interventricular delay from a plurality of predetermined interventricular delay values based on at least the activity level.

45. The method of claim 41, wherein dynamically adjusting the one or more pacing parameters further comprises dynamically selecting one or more pacing channels from a plurality of predetermined pacing channels based on at least the activity level.

46. The method of claim 37, wherein dynamically adjusting the one or more pacing parameters comprises comparing the activity level to one or more predetermined threshold levels and adjusting the one or more pacing parameters based on at least the result of the comparison.

47. The method of claim 37, wherein executing the dynamic pacing algorithm comprises:
timing a predetermined time period starting when the signal indicative of the myocardial infarction event is detected; and
starting to execute the dynamic pacing algorithm upon an expiration of the predetermined time period.

48. The method of claim 37, wherein detecting the signal indicative of the myocardial infarction event comprises receiving an external activation command from an external system communicating to the implantable pacemaker, the external activation command being the signal indicative of the myocardial infarction event.

49. The method of claim 48, further comprising receiving values for the one or more pacing parameters from the external system.

50. The method of claim 37, wherein detecting the signal indicative of the myocardial infarction event comprises detecting an ischemia.

51. The method of claim 50, wherein detecting the ischemia comprises detecting the ischemia from the at least one electrogram.

52. The method of claim 50, wherein detecting the ischemia comprises sensing an impendance.

53. The method of claim 50, wherein detecting the ischemia comprises sensing an acceleration indicative of a cardiac wall motion.

54. The method of claim 37, further comprising sensing a signal indicative of hemodynamic performance.

55. The method of claim 54, further comprising adjusting the one or more pacing parameters based on the signal indicative of hemodynamic performance.

56. The method of claim 54, wherein sensing the signal indicative of hemodynamic performance comprises sensing a signal indicative of minute ventilation.

57. The method of claim 54, wherein sensing the signal indicative of hemodynamic performance comprises sensing heart sounds, detecting first heart sounds (S1), and measuring one or more of an S1 amplitude and an S1 duration.

58. The method of claim 54, wherein sensing the signal indicative of hemodynamic performance comprises sensing heart sounds, detecting third heart sounds (S3), and measuring an S3 amplitude.

59. The method of claim 54, wherein sensing the signal indicative of hemodynamic performance comprises sensing a signal indicative of a left ventricular pressure and calculating an maximum positive derivative of the left ventricular pressure, LV+dp/dt.

60. The method of claim 54, wherein sensing the signal indicative of hemodynamic performance comprises sensing a signal indicative of stroke volume.

61. The method of claim 54, further comprising transmitting the at least one electrogram, the activity level, and the signal indicative of hemodynamic performance to an external system communicating with the implantable pacemaker via telemetry.

62. A cardiac pacing method, comprising:
sensing an activity level;
comparing the activity level to a predetermined threshold;
executing a cardiac resynchronization therapy (CRT) pacing algorithm if the activity level exceeds the predetermined threshold; and
executing a remodeling control therapy (RCT) pacing algorithm if the activity level does not exceed the predetermined threshold.

63. The method of claim 62, wherein sensing the activity level comprises sensing an acceleration.

64. The method of claim 62, wherein sensing the activity level comprises sensing a minute ventilation.

65. The method of claim 62, wherein sensing the activity level comprises sensing a heart rate.

66. The method of claim 62, wherein:
executing the CRT pacing algorithm comprises selecting a first set of pacing parameter values; and
executing the RCT pacing algorithm comprises selecting a second set of pacing parameter values.

67. The method of claim 66, wherein:
selecting the first set of pacing parameter values comprises selecting a first set of one or more pacing sites; and
selecting the second set of pacing parameter values comprises selecting a second set of one or more pacing sites.

68. The method of claim 66, wherein:
selecting the first set of pacing parameter values comprises setting at least one atrioventricular delay to a first time interval; and
selecting the second set of pacing parameter values comprises setting the at least one atrioventricular delay to a second time interval,
wherein the first time interval is longer than the second time interval.

69. The method of claim 68, wherein further comprising determining the second time interval for an optimal left ventricular stress distribution.

70. The method of claim 69, wherein further comprising determining the first time interval for a maximum positive derivative of the left ventricular pressure, LV+dp/dt.

71. The method of claim 69, wherein further comprising determining the first time interval for a maximum stroke volume.

* * * * *